US012383297B2

(12) United States Patent
Nakano et al.

(10) Patent No.: US 12,383,297 B2
(45) Date of Patent: Aug. 12, 2025

(54) MEDICAL DEVICE

(71) Applicant: TERUMO KABUSHIKI KAISHA, Tokyo (JP)

(72) Inventors: Taiga Nakano, Irvine, CA (US); Kosuke Nishio, Irvine, CA (US); Vivian Tran, Irvine, CA (US); Dan Bao, Irvine, CA (US); Lam Cang, Irvine, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 551 days.

(21) Appl. No.: 17/840,694

(22) Filed: Jun. 15, 2022

(65) Prior Publication Data

US 2022/0304722 A1 Sep. 29, 2022

Related U.S. Application Data

(63) Continuation of application No. PCT/JP2019/051518, filed on Dec. 27, 2019.

(51) Int. Cl.
*A61B 17/3207* (2006.01)

(52) U.S. Cl.
CPC ...... *A61B 17/320758* (2013.01); *A61B 2217/005* (2013.01)

(58) Field of Classification Search
CPC ...... A61B 17/320758; A61B 2217/005; A61B 2017/00685; A61B 17/3207;

(Continued)

(56) References Cited

U.S. PATENT DOCUMENTS 8,394,078 B2   3/2013 Torrance et al.
2006/0263744 A1* 11/2006 Nakanishi .......... A61B 90/92
                                                    433/165

(Continued)

FOREIGN PATENT DOCUMENTS

JP   2005328971 A   12/2005
WO   2018052121 A1   3/2018

(Continued)

OTHER PUBLICATIONS

International Search Report (PCT/ISA/210) with translation and Written Opinion (PCT/ISA/237) mailed on Mar. 24, 2020, by the Japanese Patent Office as the International Searching Authority for International Application No. PCT/JP2019/051518. (8 pages).

(Continued)

*Primary Examiner* — Mohamed G Gabr
*Assistant Examiner* — Aman Kumar Mann
(74) *Attorney, Agent, or Firm* — BUCHANAN INGERSOLL & ROONEY PC

(57) ABSTRACT

A medical device that cuts an object in a body lumen includes: a drive shaft; a shaft portion connected to the drive shaft; a cutting portion connected to the shaft portion; and first and second bearings that rotatably support the shaft portion. The first bearing has a ring shape, the second bearing has a ring shape and is spaced from a proximal side of the first bearing. The shaft portion includes a first sliding portion slidably supported by the first bearing, a second sliding portion slidably supported by the second bearing, and an intermediate portion between the first and second sliding portions. The intermediate portion has a protruding portion protruding radially outward, the protruding portion is disposed between the first bearing (81) and the second bearing in an axial direction, and the shaft portion has a (Continued)

passage that communicates from the first sliding portion to the second sliding portion).

19 Claims, 4 Drawing Sheets

(58) Field of Classification Search
CPC ...... A61B 17/32037; A61B 17/320016; A61B 17/32002; A61B 2017/320032; F16C 1/28; F16C 19/06; F16C 19/183; F16C 19/507; F16C 1/265
See application file for complete search history.

(56) References Cited

U.S. PATENT DOCUMENTS

| | | | | |
|---|---|---|---|---|
| 2011/0118660 | A1* | 5/2011 | Torrance | A61B 17/320758 604/35 |
| 2011/0208222 | A1* | 8/2011 | Ljahnicky | A61B 17/320758 606/159 |
| 2012/0083815 | A1* | 4/2012 | Troendle | A61B 17/32002 606/170 |
| 2015/0258258 | A1* | 9/2015 | Bonnette | A61M 25/0023 606/159 |
| 2018/0317952 | A1* | 11/2018 | Jamous | A61B 17/32002 |
| 2019/0201050 | A1* | 7/2019 | Nishio | A61B 17/320725 |
| 2020/0015844 | A1 | 1/2020 | Nishio et al. | |
| 2020/0191196 | A1 | 6/2020 | Nishio | |

FOREIGN PATENT DOCUMENTS

| | | |
|---|---|---|
| WO | 2018181521 A1 | 10/2018 |
| WO | 2019049736 A1 | 3/2019 |

OTHER PUBLICATIONS

English Translations of the International Search Report (Form PCT/ISA/210) and the Written Opinion of the International Searching Authority (Form PCT/ISA/237) issued Mar. 24, 2020, by the Japanese Patent Office in corresponding International Application No. PCT/JP2019/051518. (5 pages).

Office Action (Notice of Reasons for Refusal) issued on Mar. 4, 2024, in corresponding Japanese Patent Application No. 2023-121599 and English translation of the Office Action. (6 pages).

* cited by examiner

MEDICAL DEVICE

CROSS-REFERENCES TO RELATED APPLICATIONS

This application is a continuation of International Application No. PCT/JP2019/051518 filed on Dec. 27, 2019, the entire content of which is incorporated herein by reference.

TECHNOLOGICAL FIELD

This disclosure relates to a medical device for cutting an object in a body lumen.

BACKGROUND DISCUSSION

Examples of a treatment method for a stenosed site caused by a thrombus, a plaque, a calcified lesion, and the like in a blood vessel include dilating the blood vessel by using a balloon, and causing a mesh-shaped or coil-shaped stent to indwell the blood vessel as a support for the blood vessel. However, in these methods, it is difficult to treat a stenosed site that is hardened by calcification or a stenosed site that is formed at a bifurcated portion in the blood vessel. A method that can perform treatment in such a case includes cutting and removing the stenosed site such as a thrombus, a plaque, or a calcified lesion.

For example, U.S. Pat. No. 8,394,078 describes a device in which a cutting portion that cuts a stenosed site in a blood vessel is disposed at a distal end of a drive shaft. This device has a function of aspirating a cut object.

SUMMARY

The device described in U.S. Pat. No. 8,394,078 includes a ball bearing on a proximal side of the cutting portion in order to support the rotating cutting portion. The ball bearing includes a large number of balls arranged in a circumferential direction in order to smoothly rotate the cutting portion. Therefore, it is difficult to dispose a passage for aspirating the object in a portion where the ball bearing is disposed. Therefore, an inlet for aspirating the cut object from an outside into the device is disposed on the proximal side with respect to the ball bearing. Therefore, this device cannot efficiently aspirate the cut object.

The medical device disclosed here is capable of efficiently aspirating an object cut by a rotating cutting portion and maintaining a stable rotation axis.

The medical device includes: a drive shaft that is rotatable; a shaft portion that is connected to a distal portion of the drive shaft; a cutting portion connected to a distal portion of the shaft portion or the distal portion of the drive shaft; an outer tube shaft that rotatably accommodates the drive shaft; and a first bearing and a second bearing that are accommodated in the outer tube shaft and rotatably support the shaft portion, in which the first bearing has a ring shape, the second bearing has a ring shape and is disposed away from a proximal side of the first bearing, the shaft portion includes a first sliding portion slidably supported on an inner peripheral surface of the first bearing, a second sliding portion slidably supported on an inner peripheral surface of the second bearing, and an intermediate portion disposed between the first sliding portion and the second sliding portion, the intermediate portion has at least one protruding portion protruding outward in a radial direction, the protruding portion is disposed between a proximal surface of the first bearing and a distal surface of the second bearing in an axial direction, and the shaft portion has a passage that communicates from the first sliding portion to the second sliding portion.

In the medical device configured as described above, since an aspiration force can be applied to a distal side through the passage disposed inside the bearings, an external object can be aspirated inside on a distal side with respect to the bearings and the shaft portion. Therefore, the medical device can efficiently aspirate the object cut by the cutting portion. In addition, since the shaft portion is supported at two positions of the first bearing and the second bearing, stable rotation can be maintained. In addition, the first bearing and the second bearing can support the protruding portion by sandwiching the protruding portion therebetween in the axial direction. Therefore, when the medical device is pushed and pulled, a force in an axial direction applied from the shaft portion is received by the first bearing and/or the second bearing. Therefore, the medical device can maintain a stable rotation axis even when the shaft portion receives a force in a radial direction or the axial direction.

According to another aspect, a medical device positionable inside a body lumen to cut an object in the body lumen includes: an outer tubular shaft extending in the axial direction; a rotatable drive shaft positioned in the outer tubular shaft; a shaft portion connected to the drive shaft so that rotation of the drive shaft results in rotation of the shaft portion; and a ring-shaped first bearing and a ring-shaped second bearing that both rotatably support the shaft portion. The first bearing possesses an inner peripheral surface facing the outer peripheral surface of the shaft portion and an outer peripheral surface facing the inner peripheral surface of the outer tubular shaft, and the second bearing possesses an inner peripheral surface facing the outer peripheral surface of the shaft portion and an outer peripheral surface facing the inner peripheral surface of the outer tubular shaft. A cutting portion is connected to and rotatable together with the shaft portion or the drive shaft, and the cutting portion is distal of the first and second bearings. The proximal end surface of the ring-shaped first bearing and the distal end surface of the ring-shaped second bearing face one another and are spaced apart from one another in the axial direction. The shaft portion includes an intermediate portion positioned between the proximal end surface of the ring-shaped first bearing and the distal end surface of the ring-shaped second bearing, and the intermediate portion of the shaft portion possesses a distal end surface facing the proximal end surface of the ring-shaped first bearing and a proximal end surface facing the distal end surface of the ring-shaped second bearing. A groove is provided in the outer peripheral surface of the shaft portion to aspirate the object cut by the cutting portion. The groove possesses an open distal end and an open proximal end that are spaced apart from one another in the axial direction, the inner peripheral surface of the ring-shaped first bearing faces towards and overlies an axially extending first portion of the groove, and the inner peripheral surface of the ring-shaped second bearing faces towards and overlies an axially extending second portion of the groove.

Another aspect involves a method of cutting an object in a body lumen. The method comprises introducing a cutting portion of a medical device into a body lumen, wherein the medical device also includes: a rotatable drive shaft; a shaft portion connected to the rotatable drive shaft; an outer tubular shaft rotatably accommodating the drive shaft; a cutting portion connected to the distal portion of the shaft portion or the distal portion of the drive shaft; and a ring-shaped first bearing and a ring-shaped second bearing both accommodated in the outer tubular shaft and rotatably supporting the shaft portion, with the ring-shaped first bearing and the ring-shaped second bearing being spaced apart from one another in the axial direction so that a space exists between the proximal end surface of the ring-shaped first bearing and the distal end surface of the ring-shaped second bearing. The method also involves moving the cutting portion toward and into contact with the object in the body lumen, and cutting the object in the living body by rotating the cutting portion while the cutting portion is in contact with the object in the body lumen to produce cut parts of the object. The ring-shaped first bearing and a first portion of the outer peripheral surface of the shaft portion and the ring-shaped second bearing and a second portion of the outer peripheral surface of the shaft portion function as radial load bearings that receive a radial load during the cutting of the object in the living body. The ring-shaped first bearing, the ring-shaped and a portion of the shaft portion located between the proximal end surface of the ring-shaped first bearing and the distal end surface of the ring-shaped second bearing function as axial load bearings that receive an axial load during the cutting of the object in the living body. The method further comprises aspirating at least some of the cut parts of the object through a passage that is formed in the outer peripheral surface of the outer shaft and that extends from distal of a distal end surface of the ring-shaped first bearing to proximal of a proximal end surface of the ring-shaped second bearing.

BRIEF DESCRIPTION OF THE DRAWINGS

FIGS. 4A-4C show the distal portion of the medical device, in which FIG. 4A is a cross-sectional view taken along the section line A-A in FIG. 3, FIG. 4B is a cross-sectional view taken along the section line B-B in FIG. 3, and FIG. 4C is a cross-sectional view taken along the section line C-C in FIG. 3.

DETAILED DESCRIPTION

Figure 1:
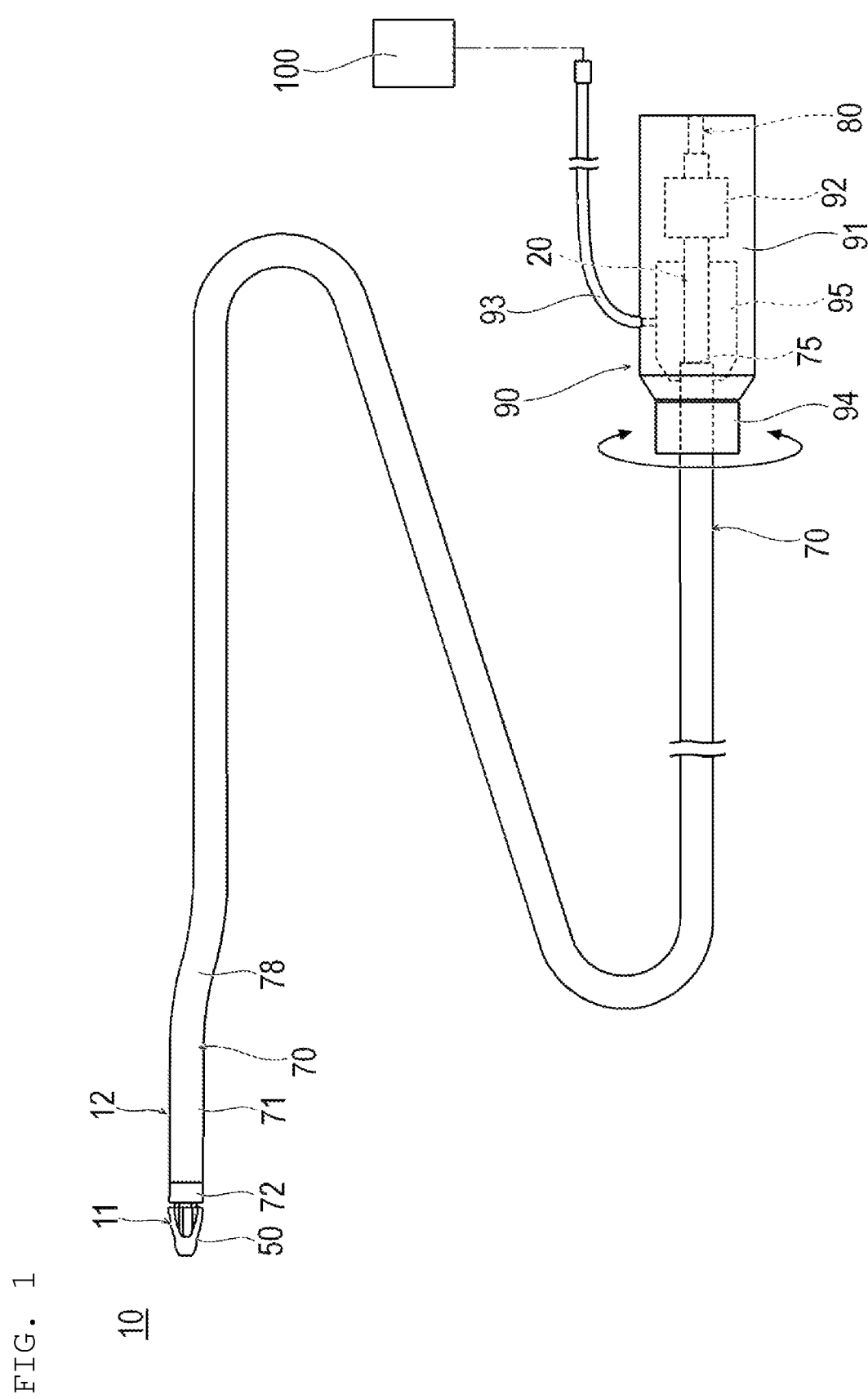
FIG. 1 is a plan view showing a medical device according to an embodiment.

Set forth below with reference to the accompanying drawings is a detailed description of embodiments of a medical device representing examples of the medical device disclosed here. The dimensions or scales on the drawings may be exaggerated or different from actuality/reality for convenience of description and illustration. For convenience of explanation, dimensions in the drawings may be exaggerated and may be different from actual dimensions. In addition, in the present description and the drawings, structural elements that have substantially the same function are denoted with the same reference numerals, and repeated explanation of these structural elements is omitted. In the present description, a side to be inserted into a lumen is referred to as a "distal side", and a side to be operated is referred to as a "proximal side".

A medical device 10 according to an embodiment is inserted into a blood vessel, and is used for a procedure for cutting and removing a plaque, a calcified lesion, and the like in an acute lower limb ischemia or a deep vein thrombosis. An object to be cut by the medical device is not particularly limited, and may be, for example, an atheroma and a thrombus. Further, all the objects that may be present in the body lumen may be objects to be cut by the medical device 10.

Figures 2, 3:
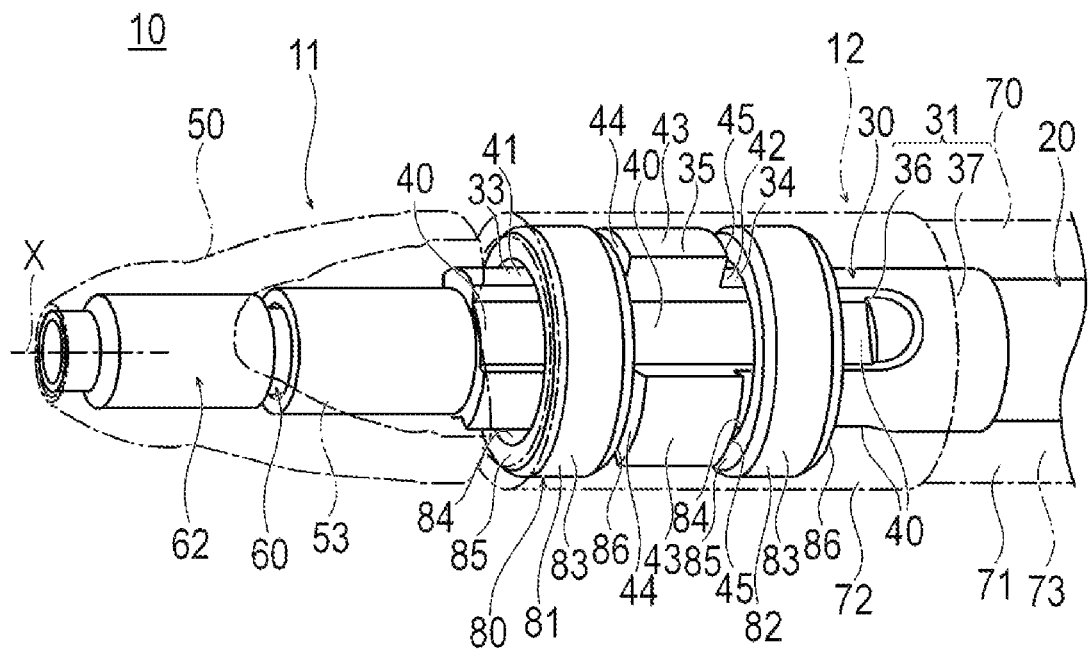
FIG. 2 is a perspective view showing a distal portion of the medical device as seen through a cutting portion and an accommodation portion.
FIG. 3 is a cross-sectional view showing the distal portion of the medical device.

As shown in FIGS. 1 to 3, the medical device 10 includes a rotation structure portion 11 that is rotatable, an accommodation portion 12 that rotatably accommodates the rotation structure portion 11, and a handle portion 90 that is operated by an operator. The rotation structure portion 11 includes a drive shaft 20 that transmits a rotational force, a shaft portion 30 that is rotatably supported by the accommodation portion 12, a cutting portion 50 that cuts a plaque or a calcified lesion, and a protective tube 60 that is accommodated in the drive shaft 20. The accommodation portion 12 includes an outer tubular shaft 70 that accommodates the drive shaft 20, and a bearing 80 that rotatably supports the shaft portion 30.

The drive shaft 20 is an elongated tube body. The drive shaft 20 is flexible and has a characteristic capable of transmitting a rotational force acting from the proximal side to the distal side. The shaft portion 30 is fixed to a distal portion of the drive shaft 20. The drive shaft 20 is a tubular body in which a plurality of wire rods are arranged around an axis X of the rotation structure portion 11 and interlocked in a spiral shape. The axis X is a structural central axis of the rotation structure portion 11 and is a central axis of the rotation structure portion 11. A proximal portion of the drive shaft 20 is located inside the handle portion 90. The drive shaft 20 may be configured or constructed in a way that does not include the wire rods.

A constituent material from which the drive shaft 20 is fabricated is not particularly limited, and may be for example, stainless steel, nitinol, fluoropolymers such as polytetrafluoroethylene (PTFE) and an ethylene tetrafluoroethylene copolymer (ETFE), polyether ether ketone (PEEK), polyimides, polyolefins such as polyethylene and polypropylene, polyamides, and polyesters such as polyethylene terephthalate.

As shown in FIGS. 1 to 3, the cutting portion 50 is a member that cuts and reduces the object (size of the object) such as a plaque or a calcified lesion. Therefore, the "cut" means applying a force to the object in contact to make the object smaller. A method for applying the force to perform the cutting and a shape or a form of the object after the cutting are not limited.

The cutting portion 50 has a large number of minute abrasive grains on a surface thereof. Alternatively, the cutting portion 50 may include a sharp blade. The cutting portion 50 is formed with a first through-hole 51 located on a distal side and a second through-hole 52 located on a proximal side of the first through-hole 51. The first through-hole 51 and the second through-hole 52 communicate with each other and penetrate or pass through the cutting portion 50 in a direction along the axis X. A distal portion of the shaft portion 30 is fitted into and interlocked with an inside of the second through-hole 52.

An outer peripheral surface of the cutting portion 50 has groove-shaped cutout portions 53 extending in the direction along the axis X. The cutout portions 53 function as flow paths for conveying the cut object in a proximal direction. The cutout portions 53 are arranged, for example, at an interval of 120 degrees in a circumferential direction. Therefore, the cutting portion 50 has three cutout portions 53 uniformly arranged in the circumferential direction. An edge portion of each cutout portion 53 is smoothly formed with a curvature. The number of the cutout portions 53 is not limited to three.

A constituent material from which the cutting portion 50 may be fabricated preferably has sufficient strength to cut a plaque, a calcified lesion, or the like, and examples of suitable material include stainless steel, nitinol, Ta, Ti, Pt, Au, W, brass, a shape memory alloy, and a cemented carbide. When a soft material such as a thrombus is to be cut, fluoropolymers such as polytetrafluoroethylene (PTFE) or an ethylene tetrafluoroethylene copolymer (ETFE), polyether ether ketone (PEEK), polyimides, polyolefins such as polyethylene and polypropylene, polyamides, polyesters such as polyethylene terephthalate, and the like can be suitably used.

The protective tube 60 is a flexible tubular body disposed inside the drive shaft 20 and the cutting portion 50. The protective tube 60 is rotatable relative to the drive shaft 20 and the cutting portion 50. The protective tube 60 is formed with a guide wire lumen 61 through which a guide wire passes. The protective tube 60 prevents the guide wire passing through the inside of the drive shaft 20 from coming into direct contact with the drive shaft 20 and rubbing against the drive shaft 20. A distal portion of the protective tube 60 is interlocked with a tubular protective tube stopper 62. A proximal portion of the protective tube stopper 62 has an outer diameter larger than that of the protective tube 60, and covers the distal portion of the protective tube 60. A distal portion of the protective tube stopper 62 has an outer diameter smaller than that of the proximal portion of the protective tube stopper 62, and protrudes toward the distal side with respect to the protective tube 60. The proximal portion of the protective tube stopper 62 is rotatably disposed in a gap between the shaft portion 30 and the cutting portion 50 in an axial direction. Therefore, the protective tube stopper 62 can rotate while being restricted from moving in the axial direction between the shaft portion 30 and the cutting portion 50. Therefore, movement of the protective tube 60 in the axial direction can be restricted by the protective tube stopper 62, and falling-off of the protective tube 60 can be suppressed.

As shown in FIGS. 2, 3 and 4A-4C, the shaft portion 30 is a portion that rotatably supports the rotation structure portion 11 with respect to the accommodation portion 12. The shaft portion 30 includes a proximal interlock portion 31 interlocked with the drive shaft 20 and a distal interlock portion 32 interlocked with the cutting portion 50. The shaft portion 30 further includes a first sliding portion 33 supported by a first bearing 81, a second sliding portion 34 supported by a second bearing 82, and an intermediate portion 35 disposed between the first sliding portion 33 and the second sliding portion 34. The shaft portion 30 is formed with at least one passage 40 (three in the present embodiment) extending along the axis X.

The proximal interlock portion 31 is a cylindrical portion disposed at a proximal portion of the shaft portion 30. The proximal interlock portion 31 includes a proximal fitting portion 37 into which the distal portion of the drive shaft 20 is fitted from the proximal side, and a proximal stepped portion 36 against which a distal surface of the drive shaft 20 abuts. The proximal stepped portion 36 is a portion whose inner diameter decreases stepwise from the proximal fitting portion 37 toward the distal side. An inner diameter of the proximal fitting portion 37 is substantially equal to an outer diameter of the distal portion of the drive shaft 20. The distal surface of the drive shaft 20 is attached to the proximal stepped portion 36. Therefore, the shaft portion 30 is fixed at an appropriate position with respect to the drive shaft 20. The proximal interlock portion 31 is joined to the drive shaft 20 by welding or the like at a plurality of positions in a circumferential direction. Since the proximal interlock portion 31 has a tubular shape, the proximal interlock portion 31 can be firmly fixed to the drive shaft 20 by surrounding the drive shaft 20. The proximal interlock portion 31 may be disposed inside the drive shaft 20 instead of outside the drive shaft 20. In addition, a proximal surface of the proximal interlock portion 31 may abut against the distal surface of the drive shaft 20.

The distal interlock portion 32 includes a distal fitting portion 38 fitted inside the second through-hole 52 of the cutting portion 50, and a distal stepped portion 39 against which a proximal surface of the cutting portion 50 abuts. The distal stepped portion 39 is a portion whose inner diameter increases stepwise from the distal fitting portion 38 toward the proximal side. An outer diameter of the distal fitting portion 38 is substantially equal to an outer diameter of the second through-hole 52 of the cutting portion 50. The proximal surface of the cutting portion 50 is attached to the distal stepped portion 39. Therefore, the cutting portion 50 is fixed at an appropriate position with respect to the shaft portion 30.

The first sliding portion 33 is a portion that is disposed on a proximal side of the distal interlock portion 32 and is rotatably supported by the first bearing 81. The three groove-shaped passages (grooves) 40 extending in an axial direction are formed on an outer peripheral surface of a circular tube of the first sliding portion 33 having a uniform outer diameter. The first sliding portion 33 includes three first rotational contact portions 41 that are in contact with an inner peripheral surface of the first bearing 81 between the three groove-shaped passages 40 equally arranged in a circumferential direction. Outer diameters of the first rotational contact portions 41 are slightly smaller than an inner diameter of the first bearing 81. Therefore, the first rotational contact portions 41 are slidably in contact with the inner peripheral surface of the first bearing 81.

The second sliding portion 34 is a portion that is disposed on a distal side of the proximal interlock portion 31 and is rotatably supported by the second bearing 82. The three groove-shaped passages 40 extending in the axial direction are formed on an outer peripheral surface of a circular tube of the second sliding portion 34 having a uniform outer diameter. The second sliding portion 34 includes three second rotational contact portions 42 that are in contact with an inner peripheral surface of the second bearing 82 between the three groove-shaped passages 40 equally arranged in the circumferential direction. Outer diameters of the second rotational contact portions 42 are slightly smaller than an inner diameter of the second bearing 82. Therefore, the second rotational contact portions 42 are slidably in contact with the inner peripheral surface of the second bearing 82.

The intermediate portion 35 is disposed between the first sliding portion 33 and the second sliding portion 34. The three groove-shaped passages 40 extending along the axis X are formed on an outer peripheral surface of a circular tube of the intermediate portion 35 having a uniform outer diameter. The intermediate portion 35 has three protruding portions 43 that protrude outward in a radial direction from the first sliding portion 33 and the second sliding portion 34 between the three groove-shaped passages 40 equally arranged in the circumferential direction. Each of the protruding portions 43 includes a protruding distal surface 44 and a protruding proximal surface 45. The three protruding distal surfaces 44 are disposed on the same plane orthogonal to the axis X. The three protruding proximal surfaces 45 are disposed on the same plane orthogonal to the axis X.

Figure 4A:
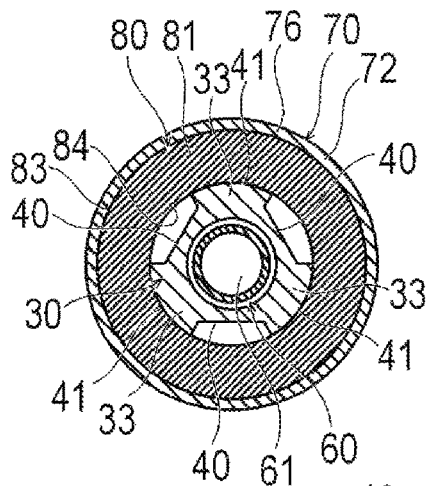
Figure 4C:
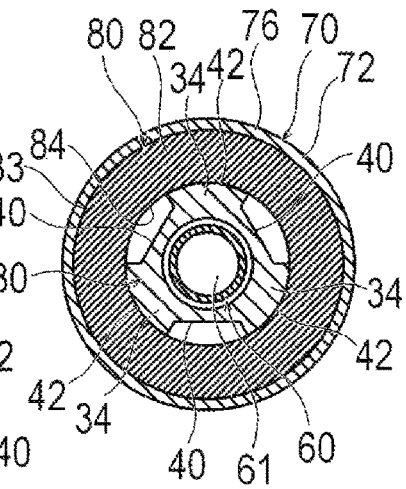
Figure 4B:
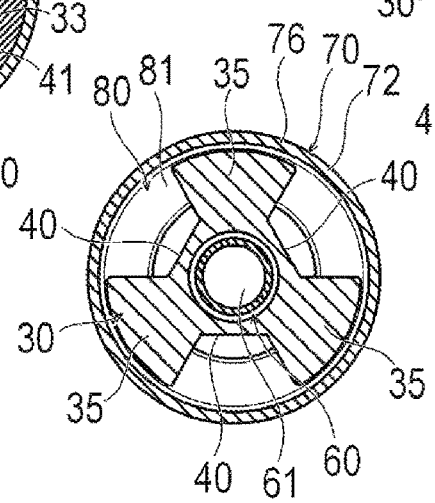

The passages 40 have open distal and proximal ends, and form flow paths for aspirating the object cut by the cutting portion 50. Distal portions of the passages 40 communicate with proximal portions of the cutout portions 53. The passages 40 are formed from the distal stepped portion 39 disposed on the distal side with respect to a portion of the shaft portion 30 supported by the bearing 80 to the proximal side with respect to a portion of the shaft portion 30 supported by the bearing 80. That is, the passages 40 are formed from the distal side to the proximal side with respect to the bearing 80. Also, as seen in FIGS. 4A and 4B, the inner peripheral surface of the first bearing 81 faces towards and overlies an axially extending portion of each passage 40, and the inner peripheral surface of the second bearing 82 faces towards and overlies a different axially extending portion of each passage 40. The groove-shaped passages 40 may partially penetrate to an inner peripheral surface of the shaft portion 30. In the present embodiment, proximal portions of the passages 40 do not reach a proximal end of the shaft portion 30, but may reach the proximal end of the shaft portion 30. The passages 40 are connected to an outer peripheral surface of the shaft portion 30 on the distal side with respect to the bearing 80. Accordingly, spaces of the passages 40 communicate with a space outside the shaft portion 30 on the distal side with respect to the bearing 80. Further, the passages 40 are connected to the outer peripheral surface of the shaft portion 30 on the proximal side with respect to the bearing 80. Accordingly, the spaces of the passages 40 communicate with the space outside the shaft portion 30 on the proximal side with respect to the bearing 80. Therefore, the passages 40 can take in the cut object from the outside of the shaft portion 30 on the distal side with respect to the bearing 80. Then, the passages 40 can release the object taken in on the distal side with respect to the bearing 80 to the outside of the shaft portion 30 on the proximal side with respect to the bearing 80. In addition, by providing the passages 40 on the shaft portion 30, an aspiration opening portion 74 for performing aspiration can be positioned near the cutting portion 50. Further, by providing the passages 40 on the shaft portion 30, friction between the shaft portion 30 and the bearing 80 is reduced, and slidability can be improved.

The passages 40 may not be formed in a groove shape on the outer peripheral surface of the shaft portion 30, but may be formed as holes penetrating in the axial direction inside the shaft portion 30. In this case, the first rotational contact portions 41 of the first sliding portion 33 may be formed as a single ring-shaped portion. In addition, the second rotational contact portions 42 of the second sliding portion 34 may be formed as a single ring-shaped portion. In addition, the protruding portions 43 may be formed as a single ring-shaped portion. In addition, the passages 40 may be formed in a groove shape on the first sliding portion 33 and the second sliding portion 34, and may be formed as holes penetrating in the axial direction in the intermediate portion 35. In this case, the plurality of first rotational contact portions 41 and the plurality of second rotational contact portions 42 are formed, and the protruding portions 43 are formed by one ring-shaped portion.

As shown in FIGS. 1 to 3, the outer tubular shaft 70 is a tubular body that accommodates the drive shaft 20 and the protective tube 60. The outer tubular shaft 70 includes an outer tubular main body 71 and a support tube 72 fixed to a distal side of the outer tubular main body 71. An aspiration lumen 73 for aspirating an object which is obtained by cutting and reducing a plaque, a calcified lesion, or the like is formed between the outer tubular shaft 70 and the drive shaft 20. The outer tubular shaft 70 includes, at a distal end thereof, the aspiration opening portion 74 for aspirating the cut object or a liquid discharged from the drive shaft 20. The distal end of the outer tubular shaft 70 is disposed with a predetermined gap G from a proximal end of the cutting portion 50 to the proximal side. The gap G has a length exceeding 0 along the axis X when the rotation structure portion 11 is disposed closest to the proximal side with respect to the accommodation portion 12. Therefore, the distal end of the outer tubular shaft 70 is prevented from coming into contact with the cutting portion 50. The outer tubular shaft 70 includes, at a proximal end thereof, a proximal opening portion 75 that opens inside the handle portion 90.

The outer tubular main body 71 is a tubular body having flexibility. The outer tubular main body 71 extends from the handle portion 90 to the vicinity of the cutting portion 50. The outer tubular main body 71 may formed with, on a distal portion thereof, a curved portion 78 at which an extending direction of the outer tubular main body 71 changes. A proximal portion of the outer tubular main body 71 is fixed to the handle portion 90. The proximal opening portion 75 is disposed at a proximal end of the outer tubular main body 71.

The support tube 72 is a circular tube made of metal and fixed to the distal portion of the outer tubular main body 71. The support tube 72 includes a support tube main body 76 having a constant inner diameter, and a stopper 77 disposed on a distal side of the support tube main body 76 and having an inner diameter smaller than that of the support tube main body 76. The aspiration opening portion 74 is disposed at a distal end of the support tube 72. The stopper 77 is in contact with a ring-shaped or annular distal surface 85 of the first bearing 81 of the bearing 80, which will be described later. Accordingly, the stopper 77 restricts the first bearing 81 from moving toward the distal side with respect to the support tube 72 and falling off from the support tube 72. Since the stopper 77 can restrict the movement of the first bearing 81 if the stopper 77 is contactable with the ring-shaped distal surface 85 of the first bearing 81, the stopper 77 may be slightly separated from the first bearing 81. The inner diameter of the stopper 77 is preferably smaller than an outer diameter of the first bearing 81 and larger than the inner diameter of the first bearing 81. The structure of the stopper 77 is not particularly limited as long as the movement of the first bearing 81 can be restricted, and may be partially disposed in a circumferential direction, for example.

A constituent material for fabricating the outer tubular main body 71 preferably has a certain degree of strength, and examples of suitable materials include stainless steel, nitinol, Ta, Ti, Pt, Au, W, a shape memory alloy, an ABS resin, engineering plastics such as polycarbonate (PC), polymethyl methacrylate (PMMA), polyacetal (POM), polyphenylsulfone (PPSU), polyethylene (PE), a carbon fiber, or polyether ether ketone (PEEK), or a combination thereof.

A constituent material for fabricating the support tube 72 preferably has a certain degree of strength, and examples of suitable materials include stainless steel, nitinol, Ta, Ti, Pt, Au, W, a shape memory alloy, engineering plastics such as polyether ether ketone (PEEK), or a combination thereof.

As shown in FIGS. 2, 3 and 4A-4C, the bearing 80 includes the first bearing 81 and the second bearing 82 each having a ring shape. The first bearing 81 and the second bearing 82 are disposed inside the support tube 72 and are spaced apart from each other along the axis X. Each of the first bearing 81 and the second bearing 82 includes an outer peripheral surface 83 having a constant outer diameter and an inner peripheral surface 84 having a constant inner diameter. In addition, each of the first bearing 81 and the second bearing 82 includes the ring-shaped or annular distal surface 85 and a ring-shaped or annular proximal surface 86 which are disposed on a plane orthogonal to the axis X. The first bearing 81 and the second bearing 82 have the same shape, but may have different shapes. The outer peripheral surface 83 of the bearings is fixed in close contact with an inner peripheral surface of the support tube 72. The inner peripheral surface 84 of the first bearing 81 is slidable on outer peripheral surfaces of the first rotational contact portions 41. The ring-shaped or annular proximal surface 86 of the first bearing 81 is slidable with the protruding distal surface 44 of the intermediate portion 35. The inner peripheral surface 84 of the second bearing 82 is slidable with respect to outer peripheral surfaces of the second rotational contact portions 42. The ring-shaped or annular distal surface 85 of the second bearing 82 is slidable with the protruding proximal surface 45 of the intermediate portion 35. Therefore, the first bearing 81 and the first sliding portion 33 function as bearings that receive a radial load. In addition, the second bearing 82 and the second sliding portion 34 function as bearings that receive a radial load. Further, the first bearing 81, the second bearing 82, and the intermediate portion 35 function as bearings that receive an axial load.

The outer peripheral surfaces 83 of the first bearing 81 and the second bearing 82 are formed rougher than the inner peripheral surface 84 and the ring-shaped proximal surface 86 of the first bearing 81 and the inner peripheral surface 84 and the ring-shaped distal surface 85 of the second bearing 82. Since the inner peripheral surface 84 and the ring-shaped proximal surface 86 of the first bearing 81 and the inner peripheral surface 84 and the ring-shaped distal surface 85 of the second bearing 82 are surfaces that slide on other members, the surfaces are preferably smooth. Then, since the outer peripheral surfaces 83 of the first bearing 81 and the second bearing 82 are formed rougher than the inner peripheral surface 84 and the ring proximal surface 86 of the first bearing 81 and the inner peripheral surface 84 and the ring-shaped distal surface 85 of the second bearing 82, the outer peripheral surfaces 83 of the bearings are less likely to slide with respect to the inner peripheral surface of the support tube 72. Therefore, the outer peripheral surfaces 83 of the first bearing 81 and the second bearing 82 are firmly fixed to the inner peripheral surface of the support tube 72. The ring-shaped distal surface 85 of the first bearing 81 and the ring-shaped proximal surface 86 of the second bearing 82 do not slide on other members. Therefore, roughness of the ring-shaped distal surface 85 of the first bearing 81 and roughness of the ring-shaped proximal surface 86 of the second bearing 82 are not particularly limited. Since the first bearing 81 and the second bearing 82 can be manufactured by fitting into a mold, and roughness of an inner surface of the mold can vary from place to place, the outer peripheral surfaces 83 of the first bearing 81 and the second bearing 82 can be made rougher than the inner peripheral surfaces 84 of the bearings, the ring-shaped distal surfaces 85, and the ring-shaped proximal surfaces 86. In addition, by adding a polishing process to the inner peripheral surfaces 84 of the bearings, the ring-shaped distal surfaces 85, and the ring-shaped proximal surfaces 86 of the first bearing 81 and the second bearing 82, the outer peripheral surfaces 83 of the first bearing 81 and the second bearing 82 can be made rougher than the inner peripheral surfaces 84, the ring-shaped distal surfaces 85, and the ring-shaped proximal surfaces 86.

Constituent materials for fabricating the first bearing 81 and the second bearing 82 are preferably ceramics, and examples may include zirconia toughened alumina (ZTA), corundum which is also called ruby or sapphire, and alumina. In addition, only surfaces of the first bearing 81 and the second bearing 82 may be formed of ceramics. Therefore, the first bearing 81 and the second bearing 82 may be formed by coating the surfaces made of a metal material or a resin material with the ceramics. The entire surfaces of the first bearing 81 and the second bearing 82 may be coated with the ceramics, or may be partially coated with the ceramics. It is preferable that at least surfaces of the first bearing 81 and the second bearing 82 that slide on the other members are coated with the ceramics. The surfaces of the first bearing 81 and the second bearing 82 that slide on the other members are the inner peripheral surface 84 and the ring-shaped proximal surface 86 of the first bearing 81, and the inner peripheral surface 84 and the ring-shaped distal surface 85 of the second bearing 82. The constituent materials for fabricating the first bearing 81 and the second bearing 82 are not necessarily limited to the ceramics, and may be, for example, stainless steel or engineering plastics such as PEEK as long as the number of rotation and torque are not so large. In addition, the coating applied to the surfaces made of the metal material or the resin material may be a DLC coating, a titanium nitride coating, a nitriding treatment, or the like.

The shaft portion 30 may be formed integrally with the cutting portion 50. As a constituent material for fabricating the shaft portion 30, materials like those mentioned above for fabricating the first bearing 81 and second bearing 82 can be used. Therefore, for example, the first rotational contact portions 41, the second rotational contact portions 42, and the protruding portions 43 of the shaft portion 30 may be formed by applying a DLC coating, a titanium nitride coating, or a surface smoothing treatment such as a nitriding treatment to stainless steel in order to improve wear resistance. In addition, the bearing 80 may be formed integrally with the outer tubular shaft 70.

As shown in FIG. 1, the handle portion 90 includes a casing 91, a drive unit 92, an aspiration port 93, and a rotation operation unit 94.

The proximal portion of the outer tubular main body 71 is fixed to a distal portion of the casing 91. An aspiration space 95 communicating with the aspiration port 93 is formed inside the casing 91. The proximal opening portion 75 of the outer tubular main body 71 is rotatably disposed in the aspiration space 95.

The rotation operation unit 94 is a portion operated by an operator with fingers thereof to apply a rotation torque to the outer tubular shaft 70. The rotation operation unit 94 is rotatably interlocked with the distal portion of the casing 91. The rotation operation unit 94 is fixed to an outer peripheral surface of the proximal portion of the outer tubular main body 71.

The drive unit 92 is, for example, a hollow motor. The drive unit 92 is rotated by a battery or electric power supplied from an outside. The drive shaft 20 is fixed to a hollow drive rotor of the hollow motor. A rotation speed of the drive unit 92 is not particularly limited, but may be, for example, 5,000 rpm to 200,000 rpm. The configuration of the drive unit 92 is not particularly limited.

The aspiration port 93 can be connected to an aspiration source 100 such as an external aspiration pump. The aspiration port 93 is aspirated by the aspiration source 100, and conveys an object, a liquid, or the like inside the aspiration space 95 toward the aspiration source 100. A pump, a syringe, or the like may be used as the aspiration source 100 as long as an aspiration pressure can be generated.

Next, a method of using the medical device 10 according to the present embodiment will be described using, as an example, a case in which a lesion area such as a plaque or a calcified lesion in a blood vessel is cut and aspirated.

Figure 5:
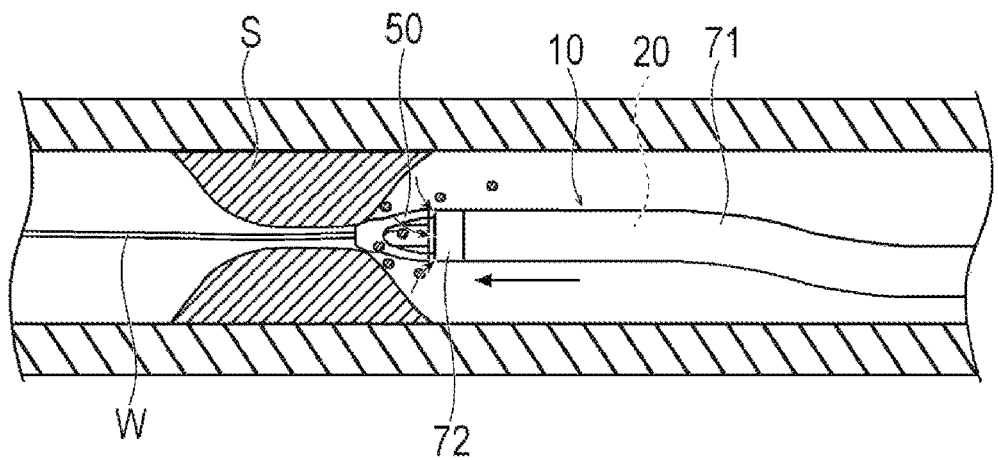
FIG. 5 is a schematic view showing a state in which cutting is performed by the medical device.

First, the operator inserts a guide wire W into the blood vessel and causes the guide wire W to reach the vicinity of a lesion area S. Next, the operator inserts a proximal end of the guide wire W into the guide wire lumen 61 of the medical device 10. Thereafter, as shown in FIG. 5, the cutting portion 50 is moved to the vicinity of the lesion area S by using the guide wire W as a guide.

Next, the operator operates the aspiration source 100. At the same time or after a certain period of time has elapsed, the drive unit 92 is operated. Accordingly, the drive shaft 20 rotates, and the cutting portion 50 and the shaft portion 30 rotate together with the drive shaft 20. Accordingly, the operator can cut the lesion area S by the cutting portion 50.

When the shaft portion 30 rotates, as shown in FIGS. 3 and 4, the first rotational contact portions 41 of the shaft portion 30 slide on the inner peripheral surface 84 of the first bearing 81, and the second rotational contact portions 42 slide on the inner peripheral surface 84 of the second bearing 82. That is, the bearing 80 receives and supports the radial load of the shaft portion 30 at two positions of the first bearing 81 and the second bearing 82. Therefore, even if the cutting portion 50 receives a force in a radial direction at the time of cutting by the cutting portion 50, the shaft portion 30 is well supported by the bearing 80 and can rotate stably.

In addition, the operator can reciprocate the outer tubular shaft 70 along a longitudinal direction of the blood vessel by moving the entire handle portion 90 or the outer tubular shaft 70 exposed to an outside of a body. Therefore, the operator can cut the lesion area S along the longitudinal direction of the blood vessel by the cutting portion 50. When the cutting portion 50 receives a force in the proximal direction due to pushing and pulling of the medical device 10, the rotating shaft portion 30 is moved to the proximal side inside the bearing 80. Accordingly, the protruding proximal surface 45 of the protruding portions 43 of the shaft portion 30 is supported by the ring-shaped distal surface 85 while sliding with respect to the ring-shaped distal surface 85 of the second bearing 82. In addition, when the cutting portion 50 receives a force in a distal direction due to the pushing and pulling of the medical device 10, the rotating shaft portion 30 is moved to the distal side inside the bearing 80. Accordingly, the protruding distal surface 44 of the protruding portions 43 of the shaft portion 30 is supported by the ring-shaped proximal surface 86 while sliding with respect to the ring-shaped proximal surface 86 of the first bearing 81. In this way, the bearing 80 receives and supports the axial load of the shaft portion 30 at the two positions of the first bearing 81 and the second bearing 82. Therefore, even if the cutting portion 50 receives a force in the direction along the axis X at the time of cutting by the cutting portion 50, the shaft portion 30 is well supported by the bearing 80 and can rotate stably. Therefore, the cutting portion 50 can effectively cut the lesion area S.

When the operator wants to change a position of the cutting portion 50 in the circumferential direction, the operator can rotate the rotation operation unit 94 while holding the casing 91. Accordingly, a direction of the curved portion 78 of the outer tubular shaft 70 is changed, and the position of the cutting portion 50 can be changed.

The aspiration source 100 applies a negative pressure to the aspiration space 95 via the aspiration port 93. Therefore, the negative pressure acts on the aspiration lumen 73 from the proximal opening portion 75 of the outer tubular main body 71 located in the aspiration space 95. Therefore, the lesion area S cut by the cutting portion 50 results in debris and this debris is aspirated into the aspiration lumen 73 from a distal opening portion. The debris can efficiently enter the passages 40 communicating with the cutout portions 53 through the cutout portions 53 of the cutting portion 50. In addition, the debris can enter the passages 40 through the gap G between the cutting portion 50 and the support tube 72. The passages 40 may be formed in spiral shapes around the axis X. Accordingly, when the drive shaft 20 is rotated by the rotating passages 40, the rotating spiral passages 40 can function as Archimedean screws (screw pumps). Accordingly, the passages 40 can smoothly convey the object and the fluid inside the aspiration lumen 73 to the proximal side.

The debris that entered the passages 40 on the distal side with respect to the first bearing 81 moves inside the first bearing 81 and the second bearing 82 toward the proximal side. Thereafter, the debris moves from the passages 40 to an outer peripheral surface side of the shaft portion 30 on the proximal side with respect to the second bearing 82. Thereafter, the debris moves through the aspiration lumen 73 toward the proximal side, passes through the aspiration space 95 and the aspiration port 93, and is discharged to the aspiration source 100. After the cutting of the lesion area S and the aspiration of the debris are completed, the operator stops operations of the aspiration source 100 and the drive unit 92. Accordingly, the cutting of the lesion area S and the discharge of the debris are stopped. Thereafter, the operator removes the medical device 10 from the blood vessel and completes the procedure.

As described above, the medical device 10 according to the present embodiment is a medical device 10 that cuts an object in a body lumen. The medical device 10 includes: the drive shaft 20 that is rotatable; the shaft portion 30 that is connected to the distal portion of the drive shaft 20; the cutting portion 50 that is connected to the distal portion of the shaft portion 30 or the distal portion of the drive shaft 20; the outer tubular shaft 70 that rotatably accommodates the drive shaft 20; the first bearing 81 and the second bearing 82 that are accommodated in the outer tubular shaft 70 and rotatably support the shaft portion 30, in which the first bearing 81 has the ring shape, the second bearing 82 has the ring shape and is disposed away from a proximal side of the first bearing 81, the shaft portion 30 includes the first sliding portion 33 slidably supported on the inner peripheral surface of the first bearing 81, the second sliding portion 34 slidably supported on the inner peripheral surface of the second bearing 82, and the intermediate portion 35 disposed between the first sliding portion 33 and the second sliding portion 34, the intermediate portion 35 has at least one protruding portion 43 protruding outward in the radial direction, the protruding portions 43 are disposed between the ring proximal surface 86 of the first bearing 81 and the ring distal surface 85 of the second bearing 82 in the axial direction, and the shaft portion 30 has the passages 40 that communicates from the first sliding portion 33 to the second sliding portion 34.

In the medical device 10 configured as described above, the aspirate force can be applied to the distal side through the passages 40 disposed inside the bearing 80. Therefore, an external object can be aspirated to the inside on the distal side with respect to the bearing 80. Therefore, the medical device 10 can efficiently aspirate the object cut by the cutting portion 50. In addition, since the shaft portion 30 is supported at the two positions of the first bearing 81 and the second bearing 82, stable rotation can be maintained. In addition, the first bearing 81 and the second bearing 82 can support the protruding portions 43 by sandwiching the protruding portions 43 therebetween in the axial direction. Therefore, when the operator pushes and pulls the medical device 10, a force in the axial direction applied to the shaft portion 30 is received by the first bearing 81 and/or the second bearing 82. Therefore, the medical device 10 can maintain the stable rotation even when the shaft portion 30 receives a force in a radial direction or the axial direction.

In addition, a distal end of the first bearing 81 is disposed away from the cutting portion 50 toward the proximal side. Accordingly, the external object is easily aspirated into the passages 40 from a portion between the cutting portion 50 and the distal end of the first bearing 81. Therefore, the medical device 10 can efficiently aspirate the object cut by the cutting portion 50. In addition, since the rotating cutting portion 50 is not in contact with the distal end of the first bearing 81, the cutting portion 50 can smoothly rotate. In addition, it is possible to prevent the cutting portion 50 and the first bearing 81 from being damaged by contact.

In addition, the outer tubular shaft 70 includes the support tube 72, the support tube 72 includes the inner peripheral surface that holds the first bearing 81 and the second bearing 82, the support tube 72 includes the stopper 77 on the distal side with respect to the first bearing 81, and the stopper 77 protrudes inward in a radial direction and is contactable with a surface on a distal side of the first bearing 81. Accordingly, the stopper 77 prevents the first bearing 81 from coming off the support tube 72 toward the distal side. Therefore, the medical device 10 can maintain the stable rotation.

In addition, the first bearing 81 and/or the second bearing 82 have/has the outer peripheral surfaces 83 rougher than the inner peripheral surfaces 84. Accordingly, the outer peripheral surfaces 83 of the first bearing 81 and the second bearing 82 are less likely to move with respect to contact targets, and can maintain stable positions.

In addition, at least a surface of the first bearing 81 and/or the second bearing 82 that slides on the rotation structure portion 11 is made of the ceramic. Accordingly, it is possible to prevent wear of the first bearing 81 and the second bearing 82 that support the rotation structure portion 11 that rotates at a high speed.

In addition, distal surfaces and/or proximal surfaces of the protruding portions 43 are flat surfaces. Accordingly, the distal surfaces and/or the proximal surfaces of the protruding portions 43 are in smooth contact with the first bearing 81 and/or the second bearing 82. Therefore, it is possible to prevent wear of the sliding protruding portions 43 and the bearing 80.

In addition, the outer tubular shaft 70 includes the outer tubular main body 71 having an elongated tubular shape, and a distal end of the outer tubular main body 71 is attached to the second bearing 82. Accordingly, the outer tubular main body 71 prevents the second bearing 82 from moving toward the proximal side. Therefore, the medical device 10 can maintain a stable rotation axis.

In addition, the passages 40 are formed in a groove shape on the outer peripheral surfaces of the first sliding portion 33, the intermediate portion 35, and the second sliding portion 34. Accordingly, the passages 40 can be easily formed by communicating with the first sliding portion 33, the intermediate portion 35, and the second sliding portion 34. In addition, the passages 40 are easily connected to the outer peripheral surfaces on a distal side of the rotation structure portion 11 with respect to the first sliding portion 33 and on a proximal side of the rotation structure portion 11 with respect to the second sliding portion 34.

In addition, the cutting portion 50 has the groove-shaped cutout portions 53 positioned along the axis X, and the cutout portions 53 communicate with the passages 40. Accordingly, the medical device 10 can aspirate the object cut by the cutting portion 50 from the cutout portions 53 into the passages 40 with high efficiency.

This disclosure is not limited to the embodiment described above, and various modifications can be made by those skilled in the art within a scope of the technical idea of this disclosure. For example, the body lumen into which the medical device 10 is inserted is not limited to the blood vessel, and may be, for example, a vessel, a urinary duct, a bile duct, a fallopian tube, or a hepatic duct.

In addition, the aspiration port 93 may be opened to an atmospheric pressure without being connected to the aspiration source 100. Even with such a configuration, when a pressure in the body lumen is higher than the atmospheric pressure, the aspiration space 95 can aspirate the object in the body lumen.

Figure 6:
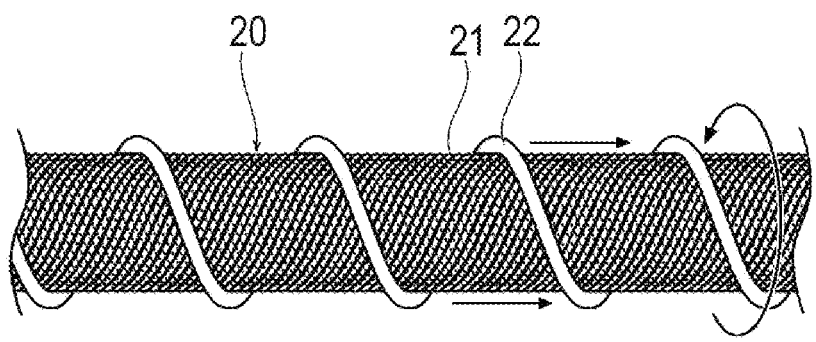
FIG. 6 is a plan view showing a drive shaft of a modification of the medical device.

In addition, as in a modification shown in FIG. 6, the drive shaft 20 may include a first layer 21 in which a plurality of wire rods are arranged around the axis X and interlocked in a spiral shape, and a spiral second layer 22 in which wire rods are sparsely wound around an outer peripheral surface of the first layer 21. When the drive shaft 20 rotates, the rotating spiral second layer 22 can function as an Archimedean screw (screw pump). Accordingly, the second layer 22 can smoothly convey the object and the fluid inside the lumen 73 to the proximal side.

In addition, the second bearing 82 may not be provided. In this case, when the rotation structure portion 11 moves in the proximal direction with respect to the accommodation portion 12, the proximal end of the cutting portion 50 is in contact with the distal end of the outer tubular shaft 70. Therefore, a distal surface of the outer tubular shaft 70 can receive the axial load.

In addition, the drive shaft 20 may be directly interlocked with the cutting portion 50 without the shaft portion 30. In this case, the shaft portion 30 can be fixed to the outer peripheral surface of the cutting portion 50 or the drive shaft 20.

In addition, central axes of the first sliding portion and the second sliding portion of the shaft portion 30 may be shifted from each other. Alternatively, a central axis of the drive shaft and a central axis of the shaft portion 30 may be shifted from each other. Alternatively, the central axis of the shaft portion 30 and a central axis of the cutting portion 50 may be shifted from each other. These methods enable the cutting portion 50 to precess, meaning the cutting portion can cut away the object by tracing a rotational path of movement larger than the outer dimension of the cutting portion. Therefore, the cutting portion 50 performing the precession can improve a cutting force.

The detailed description above describes embodiments of a medical device and operational method representing examples of the medical device and operational method disclosed here. The invention is not limited, however, to the precise embodiments, modifications and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST 10 medical device
11 rotation structure portion
12 accommodation portion
20 drive shaft
30 shaft portion
31 proximal interlock portion
32 distal interlock portion
33 first sliding portion
34 second sliding portion
35 intermediate portion
40 passage
41 first rotational contact portion
42 second rotational contact portion
43 protruding portion
44 protruding distal surface
45 protruding proximal surface
50 cutting portion
53 cutout portion
70 outer tubular shaft
71 outer tubular main body
72 support tube
73 aspiration lumen
74 aspiration opening portion
75 proximal opening portion
76 support tube main body
77 stopper
80 bearing
81 first bearing
82 second bearing
83 outer peripheral surface
84 inner peripheral surface
85 ring-shaped distal surface
86 ring-shaped proximal surface
W guide wire
X axis

What is claimed is:

1. A medical device that cuts an object in a body lumen, the medical device comprising:
   a drive shaft that is rotatable, the drive shaft possessing a distal portion;
   a shaft portion that is connected to the distal portion of the drive shaft, the shaft portion possessing a distal portion;
   a cutting portion connected to the distal portion of the shaft portion or the distal portion of the drive shaft;
   an outer tubular shaft that rotatably accommodates the drive shaft;
   a first bearing and a second bearing that are accommodated in the outer tubular shaft and rotatably support the shaft portion, the first bearing possessing an inner peripheral surface and a proximal surface, the second bearing possessing an inner peripheral surface and a distal surface;
   the first bearing being ring-shaped, the second bearing being ring-shaped and being spaced proximally from the first bearing in an axial direction;
   the shaft portion including a first sliding portion slidably supported on the inner peripheral surface of the first bearing, a second sliding portion slidably supported on the inner peripheral surface of the second bearing, and an intermediate portion disposed between the first sliding portion and the second sliding portion;
   the intermediate portion including at least one protruding portion protruding outward in a radial direction, the protruding portion being disposed between the proximal surface of the first bearing and the distal surface of the second bearing in the axial direction;
   the shaft portion including a passage that communicates from the first sliding portion to the second sliding portion; and
   the outer tubular shaft including a support tube, the support tube possessing an inner peripheral surface that holds at least the first bearing, the support tube including a stopper that protrudes inward in a radial direction on a distal side with respect to the first bearing, and the stopper being contactable with a distal end surface of the first bearing.

2. The medical device according to claim 1, wherein the first bearing possesses a distal end, the distal end of the first bearing being proximally spaced from the cutting portion.

3. The medical device according to claim 1, wherein the first bearing has an outer peripheral surface rougher than the inner peripheral surface of the first bearing and/or the second bearing has an outer peripheral surface rougher than the inner peripheral surface of the second bearing.

4. The medical device according to claim 1, wherein at least a surface of the first bearing and/or the second bearing that slides on the shaft portion is made of a ceramic.

5. The medical device according to claim 1, wherein a distal surface and/or a proximal surface of the protruding portion is a flat surface.

6. The medical device according to claim 1, wherein the outer tubular shaft includes an outer tubular main body possessing an elongated tubular shape, and a distal end of the outer tubular main body is attached to the second bearing.

7. The medical device according to claim 1, wherein the passage is a groove-shaped passage on outer peripheral surfaces of the first sliding portion, the intermediate portion, and the second sliding portion.

8. The medical device according to claim 1, wherein the cutting portion has a groove-shaped cutout portion extending along the axial direction, and the cutout portion communicates with the passage.

9. A medical device positionable inside a body lumen to cut an object in the body lumen, the medical device comprising:
   an outer tubular shaft extending in axial direction and possessing an inner peripheral surface;
   a rotatable drive shaft positioned in the outer tubular shaft;
   a shaft portion connected to the drive shaft so that rotation of the drive shaft results in rotation of the shaft portion, the shaft portion possessing an outer peripheral surface;
   a ring-shaped first bearing and a ring-shaped second bearing that both rotatably support the shaft portion, the first bearing possessing an inner peripheral surface facing the outer peripheral surface of the shaft portion and an outer peripheral surface facing the inner peripheral surface of the outer tubular shaft, the second bearing possessing an inner peripheral surface facing the outer peripheral surface of the shaft portion and an outer peripheral surface facing the inner peripheral surface of the outer tubular shaft, the ring-shaped first bearing possessing a proximal end surface and the ring-shaped second bearing possessing a distal end surface;

a cutting portion connected to and rotatable together with the shaft portion or the drive shaft, the cutting portion being distal of the first and second bearings;

the proximal end surface of the ring-shaped first bearing and the distal end surface of the ring-shaped second bearing facing one another and being spaced apart from one another in the axial direction;

the shaft portion including an intermediate portion positioned between the proximal end surface of the ring-shaped first bearing and the distal end surface of the ring-shaped second bearing, the intermediate portion of the shaft portion possessing a distal end surface facing the proximal end surface of the ring-shaped first bearing, the intermediate portion of the shaft portion possessing a proximal end surface facing the distal end surface of the ring-shaped second bearing;

a groove in the outer peripheral surface of the shaft portion to aspirate the object cut by the cutting portion, the groove possessing an open distal end and an open proximal end that are spaced apart from one another in the axial direction, the inner peripheral surface of the ring-shaped first bearing facing towards and overlying an axially extending first portion of the groove, the inner peripheral surface of the ring-shaped second bearing facing towards and overlying an axially extending second portion of the groove; and a gap between a distal end of the outer tubular shaft and a proximal end of the cutting portion, the gap being in communication with the passage to communicate the passage with an exterior of the medical device so that the object cut by the cutting portion and positioned exterior of the medical device can pass through the gap, can enter the passage and can be aspirated.

10. The medical device according to claim 9, wherein the outer tubular shaft comprises an outer tubular main body and a support tube connected to one another, the support tube possessing a distal portion at which is located a stopper that restricts the ring-shaped first bearing from moving distally with respect to the support tube, the outer tubular main body possessing a distal end, the ring-shaped second bearing being located between the distal end of the outer tubular main body and the intermediate portion of the shaft portion.

11. The medical device according to claim 9, wherein the outer tubular shaft comprises an outer tubular main body and a support tube connected to one another, the support tube possessing an inner peripheral surface in contact with the outer peripheral surface of the ring-shaped first bearing and the outer peripheral surface of the ring-shaped second bearing.

12. The medical device according to claim 9, wherein the shaft portion extends distally beyond the ring-shaped first bearing and proximally beyond the ring-shaped second bearing.

13. The medical device according to claim 9, wherein the outer tubular shaft includes a stopper that is configured to contact the ring-shaped first bearing to restrict the ring-shaped first bearing from moving distally with respect to the outer tubular shaft.

14. The medical device according to claim 9, wherein the outer peripheral surface of the first ring-shaped bearing is rougher than the inner peripheral surface of the ring-shaped first bearing and/or the outer peripheral surface of the ring-shaped second bearing is rougher than the inner peripheral surface of the ring-shaped second bearing.

15. The medical device according to claim 9, wherein the inner peripheral surface of the first ring-shaped bearing and/or the inner peripheral surface of the ring-shaped second bearing is made of a ceramic.

16. The medical device according to claim 9, wherein an outer peripheral surface of the cutting portion includes a groove-shaped cutout portion extending along the axial direction, the cutout portion being in communication with the groove in the outer peripheral surface of the shaft portion.

17. A medical device configured to be positioned in a body lumen to cut an object in the body lumen, the medical device comprising:

a drive shaft that is rotatable, the drive shaft possessing a distal portion;

a shaft portion that is connected to the distal portion of the drive shaft, the shaft portion possessing a distal portion;

a cutting portion connected to the distal portion of the shaft portion or the distal portion of the drive shaft;

an outer tubular shaft that rotatably accommodates the drive shaft;

a first bearing and a second bearing that are accommodated in the outer tubular shaft and rotatably support the shaft portion, the first bearing possessing an inner peripheral surface and a proximal surface, the second bearing possessing an inner peripheral surface and a distal surface;

the first bearing being ring-shaped, the second bearing being ring-shaped and being spaced proximally from the first bearing in an axial direction;

the shaft portion including a first sliding portion slidably supported on the inner peripheral surface of the first bearing, a second sliding portion slidably supported on the inner peripheral surface of the second bearing, and an intermediate portion disposed between the first sliding portion and the second sliding portion;

the intermediate portion including at least one protruding portion protruding outward in a radial direction, the protruding portion being disposed between the proximal surface of the first bearing and the distal surface of the second bearing in the axial direction;

the shaft portion including a passage that extends in an axial direction and has a radial dimension, the passage providing communication between the first and second sliding portions;

the passage including a first passage portion and a second passage portion, the radial dimension of the first passage portion being less than the radial dimension of the second passage portion; and wherein the first passage portion axially overlaps one of the first and second bearing, and the second passage portion axially overlaps the intermediate portion at which is located the at least one protruding portion.

18. The medical device according to claim 17, wherein the first passage portion is located on a distal side of the second passage portion.

19. The medical device according to claim 17, wherein the second passage portion is located on a distal side of the first passage portion.

* * * * *